United States Patent [19]

Matuhashi et al.

[11] 4,372,883
[45] Feb. 8, 1983

[54] PROCESS FOR THE PRODUCTION OF VACCINE

[75] Inventors: Tyoku Matuhashi, Kawaguchi; Mitsuko Usui, Tokyo; Akio Yamamoto, Higashikurume; Masakazu Mitsuhashi; Shunsaku Koyama, both of Okayama, all of Japan

[73] Assignee: Kabushiki Kaisha Hayashibara Seibutsu Kagaku Kenkyujo, Okayama, Japan

[21] Appl. No.: 178,904

[22] Filed: Aug. 18, 1980

[30] Foreign Application Priority Data

Sep. 5, 1979 [JP] Japan ................................ 54-112848

[51] Int. Cl.³ ...................... A61K 39/385; C07G 7/00

[52] U.S. Cl. ............................ 260/112 R; 260/112 B; 424/88; 428/89; 424/90; 424/91; 424/92; 424/85; 424/86; 424/87; 435/7; 536/5; 536/4.1; 436/543

[58] Field of Search ....................... 260/112 R, 112 B; 424/85, 86, 87, 88, 89, 90, 91, 92, 12; 435/7; 536/5, 4

[56] References Cited

U.S. PATENT DOCUMENTS

| | | | |
|---|---|---|---|
| 3,641,235 | 2/1972 | Weiss | 260/112 B X |
| 3,645,852 | 2/1972 | Axen et al. | 260/112 R |
| 4,003,792 | 1/1977 | Mill et al. | 424/91 X |
| 4,046,722 | 9/1977 | Rowland | 260/112 B X |
| 4,057,685 | 11/1977 | McIntire | 424/92 X |
| 4,093,607 | 6/1978 | Sela et al. | 260/112 R X |
| 4,125,492 | 11/1978 | Cuatrecasas et al. | 424/92 X |
| 4,140,679 | 2/1979 | Malley | 424/91 X |
| 4,226,978 | 10/1980 | Boguslaski et al. | 435/7 X |

*Primary Examiner*—Howard E. Schain
*Attorney, Agent, or Firm*—Browdy and Neimark

[57] ABSTRACT

The present invention relates to a process for the production of vaccine, characterized by covalent attachment of a biologically toxic substance to a saccharide both to form a biologically toxic substance-saccharide conjugate and to detoxify said substance, followed by collection of the formed conjugate. According to the invention, various vaccine products having a high productivity of immunoglobulin G and M antibodies, but without productivity of immunoglobulin E antibody, are easily obtainable. In addition, the vaccine products, upon administration to animals, do not effect any allergic reaction and/or anaphylactic-shock due to the lack of the immunoglobulin E antibody production.

5 Claims, No Drawings

PROCESS FOR THE PRODUCTION OF VACCINE

DETAILED DESCRIPTION OF THE INVENTION

The present invention relates to a process for the production of vaccine, comprising covalently attaching of a biologically toxic substance to a saccharide to form a biologically toxic substance-saccharide conjugate and to detoxify said substance, and then collecting the formed conjugate.

Generally, vaccines have been prepared by detoxification or inactivation of highly-purified biologically toxic substances with a reagent, such as formalin or β-propiolactone, without decreasing their immunogenicities. Such vaccines have been used in prevention, treatment and clinical testing of various diseases. The productivity of antibodies such as immunoglobulin G and M which prevent infection are more decreased in comparison with that of intact biologically toxic substance when a vaccine is prepared according to conventional methods. And also, the administration of a vaccine disadvantageously elicits a potency to produce immunoglobulin E antibody which causes allergic reaction and/or anaphylactic-shock.

The present inventors investigated processes for the production of vaccine, by which the potency to elicit allergic reaction and/or anaphylactic-shock-causing immunoglobulin E antibody is substantially or completely eliminated without decreasing the productivity of antibodies such as immunoglobulin G and M which prevent infections. The efforts resulted in the present invention that a biologically toxic substance-saccharide conjugate, prepared by covalent attachment of said substance to a saccharide, does well fulfill the present object.

Biologically toxic substances applicable in the present invention, which generally contain a toxic protein, proteinaceous toxin and/or toxic enzymes such as collagenase or protease, include bacterial toxins such as those of diphtheria, tetanus, botulinus, gas gangrene and cholera which cause human and/or animal diseases, zootoxins including venom such as those of *Agkistrodon halys*, *Trimeresurus flavoviridis* and scorpion, and phytotoxins such as ricin.

Saccharides usable in the present invention include mono-, di-, oligo- and poly-saccharides such as starch, amylose, dextran, polysucrose (Ficoll, Registered Trade Mark of Pharmacia Fine Chemicals AB, Uppsala, Sweden), pullulan, elsinan, curdlan, gum arabic, gum tragacanth, guar gum, xanthan gum, carrageenan, pectin, cellulose, glucomannan, chitosan, and their derivatives and partial hydrolysates, having an average molecular weight in the range of about 100–10,000,000; preferably in the range of about 500–1,000,000. Especially, the covalent attachment of said biologically toxic substance to pullulan, elsinan or their partial hydrolysates advantageously detoxifies said substance, and remarkably augments the original productivity of antibodies such as immunoglobulin G and M, but on the contrary, substantially eliminates immunoglobulin E antibody production.

Any procedure can be employed in the present invention as long as the attachment of said substance to a saccharide is effected. For example, diazo coupling, peptide method, alkylation method, cross-linking and disulfide coupling are preferable.

Diazo coupling involves a coupling reaction of said substance with a diazotized saccharide bearing one or more types of aromatic amino groups chosen from the group comprising p-aminobenzyl, m-aminobenzyl, p-aminobenzoyl, m-aminobenzoyl, m-aminoanisoyl, p-aminobenzyloxy methyl, 3-(p-aminophenoxy)-2-hydroxyl-propionyl and, 3-(p-amino-m-methyl anilino)-5-chloro triazinyl groups which are introducible by conventional methods.

The peptide method involves a reaction of said substance with an activated saccharide such as BrCN-activated saccharides, sugar carbonates, acid azide, acid halide, carbodiimide and isocyanate derivatives of carboxyl group bearing saccharides.

The alkylation method involves a reaction of said substance with an alkyl halide derivative of saccharide such as those bearing a functional group chosen from the group comprising chloroacetyl, bromoacetyl, iodoacetyl and triazinyl halide groups.

The cross-linking method is carried out in the presence of said substance and a polyfunctional reagent such as glutaraldehyde, glyoxal, succindialdehyde, hexamethylene diisocyanate, toluene 2,4-diisocyanate, bisazobenzidine and N,N'-ethylene-bis-maleimide.

In respect to the weight ratio of biologically toxic substance vs. saccharide upon conjugation reaction, generally a ratio in the range of about 1:1,000–1,000:1, but preferably the range of about 1:100–100:1, is employable in the invention. In this case the biologically toxic substance and the saccharide, respectively, are not limited to one variety: either conjugation using one variety of biologically toxic substance and two or more varieties of saccharides, or that using one variety of saccharide and two or more varieties of biologically toxic substances to produce mixed vaccine, as well as using two or more respective varieties of biologically toxic substances and saccharides, is employable in the invention.

Any reaction conditions can be employable in the present invention as long as the resultant biologically toxic substance-saccharide conjugate is detoxified, and the conditions do decrease remarkably the productivity of immunoglobulin E antibody which causes allergic reaction and/or anaphylactic-shock, without substantially decreasing that of immunoglobulin G and M antibodies which prevent infections. For example, conjugation is carried out at a temperature of about 0°–100° C. and pH of about 3–12 for about 0.1–50 hours.

The biologically toxic substance-saccharide conjugate thus obtained is generally subjected to purification and separation methods such as filtration, washing, centrifugation, salting-out, dialysis, adsorption and desorption by ion exchanger, gel filtration, ion exchange chramatography, affinity chromatography and electrophoresis, and subsequent concentration into syrup or liquid or drying into powder, to obtain the vaccine product.

For desensitization or human or animal interferon induction, the vaccine product is advantageously usable alone or in combination with other substances such as antiseptic agent or adjuvant. Furthermore, while the vaccine production according to conventional method using formalin generally requires a period of 20–90 days for detoxification, there is still a fear that the potential toxicity may restore. On the other hand, although the present process generally requires only a period of 1–2 days for detoxification, the product is very stable over a long period of storage without fear for such. Thus, the provision to cope with prevalence of diseases will become considerably easier. In addition, since the vaccine production prevents lethal allergic reaction and anaphylactic-shock which are due to contaminating proteins, it does not necessarily require a highly-purified biologically toxic substances as starting material. Consequently, the present process according to the present invention enables direct detoxification of the substance without prior purification steps, and thus the cost-reduction and sufficient supply of the vaccine is easily achieved. Also, it was found that the vaccine product prepared with a crude material has an immunogenic activity comparable to or much higher than those prepared with a highly-purified one.

Several embodiments according to the present invention will be disclosed hereinafter.

EXAMPLE 1

Tetanus toxoid vaccine 1-(1). Preparation of tetanus toxin

Tetanus toxin was prepared according to the procedure as described in "Japan J. Med. Sci. Biol.", vol.14, page 121 (1961): Harbard A 47 strain was innoculated to 100 liters of P II medium, followed by a seven-day-cultivation of the resultant mixture at 35° C.

To the supernatant obtained by centrifugation of the culture broth was added 50 w/v % aqueous zinc chloride solution, and the toxin was extracted in aqueous sodium monohydrogen phosphate solution from the formed precipitate, followed by addition of ammonium sulfate to the extract to give 40–60% saturation and by subsequent collection of the formed precipitate. A crude tetanus toxin solution was prepared by dissolving the precipitate in distilled water.

Then the crude toxin was purified by applying it on dextran gel- and ion exchanger-column systems using Sephadex G-100 (Registered Trade Mark of Pharmacia Fine Chemicals AB, Uppsala, Sweden) and DEAE-cellulose respectively, whereby a highly-purified tetanus toxin having 3,000 Lf per mg protein nitrogen was obtained. One Lf unit is defined as the amount of toxin or toxoid that most rapidly effects flocculation reaction when mixed with one unit of anti-toxin.

1-(2). Preparation of tetanus toxin-pullulan conjugate

Pullulan solution, prepared with 400 ml of water and 5 g pullulan (average molecular weight about 140,000), was adjusted to pH 10.7 with 1 N sodium hydroxide. While keeping the pH at this level, to the mixture was added gradually 3 g BrCN, and the reaction was continued for one hour to activate the pullulan, followed by pH-adjustment to 5.0 with 1 N hydrochloric acid and by subsequent dialysis of the reaction mixture against chilled water at pH 5.0.

To the activated pullulan solution was added 200 ml of the highly-purified tetanus toxin solution, prepared in EXAMPLE 1-(1), and then the conjugation reaction was allowed to continue at room temperature for 24 hours. After completion of the conjugation reaction to, the reaction mixture was added three volumes of acetone, and the resultant precipitate was collected. Then the precipitate was dissolved in 0.01 M phosphate buffer (pH 7.0), and centrifuged to remove insoluble substances. The resultant supernatant was subjected to gel filtration to collect the fraction containing the toxin-pullulan conjugate, and the fraction was filtrated with Millipore-filter (Registered Trade Mark of Millipore Incorporation, Bedford, Massachusetts, U.S.A.) to obtain a tetanus toxoid vaccine in the yield of about 70% against starting toxin protein.

According to a conventional method, control vaccine was prepared by addition of pharmacopoeial formalin solution to 50 ml of the highly-purified tetanus toxin solution to a final concentration of 0.4 v/v %, and three-week-standing of the mixture at 37° C. The yield was about 60% against starting toxin protein.

1-(3). Administration test of the vaccine to animal

Administration test of the vaccine product to mice demonstrated that the toxicity of the toxin was decreased to about 1/50,000 by the conjugation, and its Minimal Lethal Dose (MLD) was about one or much higher per Lf. In addition, intravenous injection of the vaccine to mice was carried out in the amount of 10 Lf of the present and control vaccines, and was repeated with the same doses seven days later. Ten days after the last administration, the mice were bled and the antibody titers were determined. The titers of immunoglobulin G and M antibodies were determined by the Passive Haemagglutination (PHA) reaction as described in "Japan J. Med. Sci. Biol.", vol.28, page 127 (1975), and that of immunoglobulin E antibody by the Passive Cutaneous Anaphylaxis (PCA) reaction as described in "Life Science", vol.8, page 813 (1969). The assays revealed that the administration of the vaccine product prepared according to the invention leads to about 12-fold higher production of immunoglobulin G and M antibodies in comparison with those attained by the control vaccine, and that no immunoglobulin E antibody production was totally detectable.

As obvious from the above results, the conjugate is suitable as tetanus toxoid vaccine.

EXAMPLE 2

Diphtheria toxoid vaccine 2-(1). Preparation of diphtheria toxin

Diphtheria toxin was prepared according to the procedure as described in "Journal of Immunology", vol.40, pp. 21-32 (1941): Park Williams No.8 strain was innoculated to 20 liters of Mueller & Miller's medium, followed by 48-hour-cultivation of the resulting mixture at 35° C. under agitation and aerobic conditions.

After centrifugation of the culture broth, the supernatant (pH 8.4) was cooled to 4° C., and added gradually 50 w/v % aqueous zinc chloride solution to give a pH 6.0, followed by centrifugation of the mixture and by subsequent collection of the resultant precipitate. The precipitate was dissolved in one tenth volume of 25 w/v % $Na_2HPO_4.12H_2O$ solution, and the resultant solution was subjected to one-hour-standing at 35° C. and to centrifugation.

To the resultant supernatant was added 0.3 w/v % of activated carbon and ammonium sulfate to 40% saturation, and the mixture was subjected to three-hour-standing and filtration. Then, to the filtrate was added further ammonium sulfate to 60% saturation and the mixture was left to stand overnight, followed by centrifugation of the mixture and by subsequent collection of the precipitate. The precipitate was dissolved in 700 ml of M/15 phosphate buffer (pH 8.0), and subjected to ion exchange chromatography and gel filtration. Thus a diphtheria toxin (about 3,000 Lf/ml) was obtained.

2-(2). Preparation of diphtheria toxin-pullulan conjugate

An activated pullulan solution, prepared by the method as described in EXAMPLE 1-(2), was adjusted to pH 8.0 with 0.05 M carbonate buffer, followed by addition of 200 ml diphtheria toxin solution. The resulting solution was subjected to conjugation reaction at room temperature for 24 hours, and the formed toxin-pullulan conjugate was purified and separated similarly as in EXAMPLE 1-(2) to obtain a diphtheria toxoid vaccine in the yield of about 70% against starting toxin protein.

Control vaccine was prepared by addition of pharmacopoeial formalin solution to 50 ml toxin solution prepared in EXAMPLE 2-(1) to a final concentration of about 0.4 v/v %, five-week-standing at 37° C., dialysis for two days, and Millipore-filtration. The yield was about 60% against starting toxin protein.

2-(3). Administration test of the vaccine to animal

Administration of 0.02 Lf of the control vaccine, diluted with physiological saline solution, to guinea pigs (weighing about 300 g) resulted in their toxic death. In contrast, administration of the toxoid vaccine (c.a. 500 Lf) prepared according to the invention caused no death. Determination of the immunoglobulin G and M antibody titers according to the method as described in EXAMPLE 1-(3) demonstrated that the titers were increased by the conjugation to about 10-fold higher than those attained with the control, and that no immunoglobulin E antibody production was totally detectable. Also a considerable amount of immunoglobulin E antibody as well as those of immunoglobulin G and M antibodies was found after immunization with 1 ml control vaccine plus 1 mg alminium hydroxide adjuvant.

As obvious from the above results, since there was no allergic reaction and anaphylactic-shock fears in the case of administration of the present vaccine product, the product is suitable as a diphtheria toxoid vaccine.

EXAMPLE 3

Diphtheria toxoid vaccine

Elsinan solution, prepared with 200 ml hot water and 8 g elsinan (average molecular weight about 800,000), was cooled to room temperature, and then added 40 ml of 10 w/v % cyanuric chloride in dimethyl formamide, followed by activation reaction at this temperature for two hours while keeping the pH at 7.0. After completion of the reaction, the reaction mixture was dialyzed against water at 4° C. while keeping the pH at this level. Thus an activated elsinan solution was obtained.

To the solution was added 45 ml diphtheria toxin solution to effect conjugation reaction, and the reaction was continued for two hours at pH 9.0 and room temperature with stirring. The reaction mixture was purified and separated similarly as in EXAMPLE 1-(2) to obtain the toxoid vaccine in the yield of about 60% against starting toxin protein.

Administration study of the toxoid vaccine to mice according to the method as in EXAMPLE 1-(3) demonstrated that the toxin was sufficiently detoxified by the conjugation. Also determination of the immunoglobulin G and M antibody titers demonstrated that the titers were increased by the conjugation to about 10-fold higher than those attained with the control, prepared in EXAMPLE 2-(3), and that no immunoglobulin E antibody production was totally detectable.

The above results lead to the conclusion that the conjugate is suitable as diphtheria toxoid vaccine.

EXAMPLE 4

Diphtheria toxoid vaccine

A diphtheria toxoid vaccine was prepared similarly as in EXAMPLE 2-(2), except that the pullulan (average molecular weight about 140,000) was replaced by dextran (average molecular weight about 70,000). The yield was about 40% against starting toxin protein.

Administration study of the vaccine product to mice according to the method as described in EXAMPLE 1-(3) demonstrated that the toxin was sufficiently detoxified by the conjugation. Also determination of the immunoglobulin G and M antibody titers demonstrated that the titers were augmented by the conjugation to about 5-fold higher than those attained with the control, prepared in EXAMPLE 2-(3), and that no immunoglobulin E antibody production was totally detectable.

As obvious from the above results, the conjugate is suitable as diphtheria toxoid vaccine.

EXAMPLE 5

Trimeresurus flavoviridis toxoid vaccine 5-(1). Preparation of Trimeresurus flavoviridis toxin Solid Trimeresurus flavoviridis toxin was dissolved in 0.02 M Tris-HCl buffer (pH 8.5) to give a final concentration of about 5 w/v %, and the resulting mixture was centrifuged to remove insoluble substances. The supernatant was used in the following experiments as crude Trimeresurus flavoviridis toxin.

5-(2). Preparation of Trimeresurus flavoviridis toxin-partial pullulan hydrolysate conjugate Pullulan solution, prepared with 110 ml dimethyl formamide and 5.2 g of a partial pullulan hydrolysate (average molecular weight about 10,000) with heating, was cooled to room temperature, and 10 ml pyridine and 1.0 g p-nitrobenzoyl chloride was added with stirring, followed by 17-hour-standing of the resulting solution at room temperature. To the reaction mixture was added two volumes of n-propyl alcohol, and the formed precipitate was collected and dissolved in dimethyl formamide. The above precipitation procedure was repeated three times, and the precipitate obtained finally was dissolved in 100 ml of 5 w/v % sodium dithionite solution, followed by 30-minute-incubation at 80° C. The resultant was decolorized with activated carbon, and after filtration of the mixture two volumes of n-propyl alcohol was added to the filtrate. The precipitate was dissolved in water, and the resulting solution was dialyzed against water overnight, followed by cooling of the dialysate to below 2° C. and by subsequent addition of hydrochloric acid to give a final concentration of about 0.1 N. To the solution was added further sodium nitrite to a concentration of about 1 w/v % to diazotize the partial pullulan hydrolysate. After completion of diazotization reaction, the resultant was dialyzed against water at below 4° C. for two hours. Thus a diazotized partial pullulan hydrolysate was obtained.

To the diazotized partial pullulan hydrolysate solution was added 20 ml toxin solution, prepared in EXAMPLE 5-(1), followed by pH-adjustment to 8.5 with sodium carbonate. The mixture was subjected to diazo coupling reaction at 4° C. for two hours with stirring, and the reaction mixture was purified and separated similarly as in EXAMPLE 1-(2) to obtain a Trimeresurus flavoviridis toxin-partial pullulan hydrolysate conjugate in the yield of about 60% against starting toxin protein.

Control vaccine was prepared by addition of 0.05 v/v % pharmacopoieal formalin solution to the toxin solution, prepared in EXAMPLE 5-(1), 60-day-standing at 4° C. to inactivate the toxin, centrifugation, and subsequent Millipore-filtration. In this case the yield was about 50% against starting toxin protein.

5-(3). Administration test of the vaccine to animal

Administration study of the present and control vaccines to mice according to the method as described in EXAMPLE 1-(3) demonstrated that the toxin was sufficiently detoxified by the conjugation. Furthermore, determination of the immunoglobulin G and M antibody titers demonstrated an augmentation of the titers to about 5-fold higher than those attained with the control, and also no immunoglobulin E antibody production after immunization with the present vaccine product. In contrast when immunized with the control vaccine, a significant immunoglobulin E antibody production was definitely detected as well as immunoglobulin G and M antibody productions.

In view of the above results and the fact that administration of the conjugate did not effect allergic reaction and anaphylactic-shock, the conjugate is advantageously usable as *Trimeresurus flavoviridis* toxoid vaccine.

EXAMPLE 6

*Trimeresurus flavoviridis* toxoid vaccine

Elsinan solution, prepared with 200 ml distilled water and 10 g elsinan (average molecular weight about 200,000) with heating, was cooled to room temperature, followed by addition of 5 g hexamethylene diamine and by subsequent pH-adjustment to 11.0 with 1 N sodium hydroxide. Then to the solution was added gradually 5 g BrCN while stirring and maintaining the temperature below 20° C. by adding ice. The reaction was continued for 30 minutes with stirring, and then the reaction mixture was dialyzed against distilled water at 4° C. for one hour to obtain an activated elsinan solution.

To the activated elsinan solution was added 2 ml of 25 w/v % aqueous glutaraldehyde solution, 60 ml crude *Trimeresurus flavoviridis* toxin solution, prepared in EXAMPLE 5-(1), and 10 ml of 1 M acetate buffer (pH 5.0), followed by conjugation reaction at 4° C. for 24 hours with stirring, addition of glycine to give a concentration of about 1 M and subsequent 24-hour-standing at room temperature, in order to block the unreacted active groups. Then the reaction mixture was centrifuged and the resultant supernatant was applied on gel filtration to collect the fraction containing toxin-elsinan conjugate, followed by concentration of the fraction and subsequent Millipore-filtration of the resultant to obtain a *Trimeresurus flavoviridis* toxoid vaccine in the yield of about 50% against starting toxin protein.

Administration study of the vaccine product to mice according to the method as described in EXAMPLE 1-(3) demonstrated that the toxin was sufficiently detoxified by the conjugation. Furthermore, after determination of the immunoglobulin G and M antibody titers, it was found that the titers were augmented by the conjugation to about 8-fold higher than those attained with the control, prepared in EXAMPLE 5-(2), and also that no immunoglobulin E antibody production was totally detectable.

Consequently, the conjugate is suitable as *Trimeresurus flavoviridis* toxoid vaccine.

EXAMPLE 7

*Trimeresurus flavoviridis* toxoid vaccine

To an activated carboxymethyl cellulose solution, prepared by addition of 2 g 1-ethyl-3-(3-dimethylaminopropyl)-carbodiimide methiodide to 200 ml of 1 w/v % carboxymethyl cellulose solution (average molecular weight about 20,000), pH-adjustment to 4.0, activation reaction at room temperature with stirring, and dialysis of the reaction mixture against distilled water overnight, was added 50 ml toxin solution, prepared in EXAMPLE 5-(1), and the resulting mixture was adjusted to pH 4.5, and then subjected to conjugation reaction at room temperature with stirring overnight. A supernatant obtained by centrifugation of the resultant was applied on gel filtration to obtain the fraction containing a toxin-carboxymethyl cellulose conjugate, followed by concentration of the fraction and subsequent Millipore-filtration. Thus a toxoid vaccine product was obtained in the yield of about 60% against starting toxin protein.

Administration study of the vaccine to mice according to the method as described in EXAMPLE 1-(3) demonstrated that the toxin was sufficiently detoxified by the conjugation. Furthermore, after determining the immunoglobulin G and M antibody titers, there was found an increment of the titers to about 3-fold higher than those attained with the control, prepared in EXAMPLE 5-(2), and also no immunoglobulin E antibody production.

Accordingly, the conjugate is suitable as *Trimeresurus flavoviridus* toxoid vaccine.

EXAMPLE 8

Detoxified ricin 8-(1). Preparation of ricin

A crude ricin solution was prepared by extraction in 0.85 w/v % saline solution from defatted castor bean powder, centrifugation of the extract, salting-out of the resulting supernatant with ammonium sulfate at 33-50% saturation and pH 8.0, and final dissolution of the precipitate in water.

8-(2). Preparation of ricin-pullulan conjugate

To an activated pullulan solution, prepared by the method as described in EXAMPLE 1-(2), was added 200 ml crude ricin solution, prepared by the method as described in EXAMPLE 8-(1), and the resultant solution was subjected to conjugation reaction at room temperature for 24 hours to obtain a ricin-pullulan conjugate, followed by purification and separation of the formed conjugate according to the method as in EXAMPLE 1-(2). Thus a detoxified ricin was obtained in the yield of about 40% against starting ricin protein.

8-(3). Administration test of the detoxified ricin to animal

Administration study of the detoxificated ricin to mice according to the method as described in EXAMPLE 1-(3) demonstrated that ricin was sufficiently detoxified by the conjugation. In addition, repeated intravenous injection of the detoxified ricin to mice resulted in no anaphylactic-shock.

The above results do suggest the possible use of the conjugate as desensitizer or interferon inducer.

EXAMPLE 9

Detoxified ricin

An activated gum arabic was prepared similarly as in EXAMPLE 3-(2), except that the elsinan (average molecular weight about 800,000) was replaced by gum arabic (average molecular weight about 300,000). To the activated gum arabic solution was added 100 ml crude ricin, prepared in EXAMPLE 8-(1), followed by pH-adjustment of the resultant solution to 9.0 and by subsequent conjugation reaction at room temperature for two hours with stirring. The resultant ricin-gum arabic conjugate was purified and separated similarly as in EXAMPLE 1-(2). Thus a detoxified ricin was obtained in the yield of about 50% against starting ricin protein.

Administration study of the detoxified ricin to mice according to the method as described in EXAMPLE 1-(3) demonstrated that ricin was sufficiently detoxified by the conjugation. Similarly as the administration results in EXAMPLE 8-(3), repeated intravenous injection of the detoxified ricin to mice effected no anaphylactic-shock.

As obvious from the above results, the conjugate is suitable as desensitizer or interferon inducer.

EXAMPLE 10

Tetanus toxoid vaccine

To maltotriose solution, prepared with 3 g maltotriose and 300 ml distilled water, was added 15 ml of a 10 w/v % cyanuric chloride solution in dimethyl formamide, adjusted to pH 7.0, and subjected to activation reaction at room temperature for two hours with stirring. Then to the activated maltotriose solution was added 150 ml of the highly-purified tetanus toxin solution, prepared in EXAMPLE 1-(1), followed by pH-adjustment of the resultant solution to 9.0 with 1 N sodium carbonate, conjugation reaction at 4° C. with stirring, addition of 10 g glycine and subsequent 6-hour-standing at this temperature. After centrifugation of the reaction mixture, the obtained supernatant was subjected to ion exchange chramatography and gel filtration to obtain the fraction containing a tetanus toxin-matotriose conjugate which was then subjected to Millipore-filtration to obtain the tetanus toxoid vaccine in the yield of about 80 % against starting toxin protein.

Administration study of the vaccine product to mice according to the method as described in EXAMPLE 1-(3) demonstrated that the toxin was sufficiently detoxified by the conjugation. Furthermore, determination of the immunoglobulin G and M antibody titers revealed an about 16-folds higher augmentation of the titers in comparison with those attained with the control, prepared in EXAMPLE 1-(2), and also no immunoglobulin E antibody production after immunization with the present toxoid vaccine.

As obvious from the above results, the conjugate is suitable as tetanus toxoid vaccine.

What we claim is:

1. A process for the production of vaccine, consisting of the steps of:
   covalently attaching a biologically toxic substance to a saccharide selected from the group consisting of pullulan, elsinan and partial hydrolysates of pullulan or elsinan having an average molecular weight of 500 to 1,000,000, to form a biologically toxic substance-saccharide conjugate in which the biologically toxic substance is detoxified; and
   collecting the resultant conjugate.

2. A process as set forth in claim 1, wherein said biologically toxic substance is one or more members selected from the group consisting of diphtheria toxin, tetanus toxin, botulinus toxin, gas gangrene toxin, cholera toxin, *Agkistrodon halys* venom, *Trimeresurus flavoviridis* venom, scorpion zootoxin, and ricin.

3. A process as set forth in claim 1, wherein said covalent attachment is effected with a saccharide and biologically toxic substance in the weight ratio of 1:100 to 100:1, at a pH in the range from 3 to 12, and a temperature in the range from 0° to 100° C. for 0.1 to 50 hours.

4. A process in accordance with claim 1, wherein said biologically toxic substance is one or more members selected from the group consisting of bacterial toxins, zootoxins and phytotoxins.

5. A vaccine produced in accordance with the process of claim 1.

* * * * *